US00PP18155P2

(12) United States Plant Patent
Robb

(10) Patent No.: US PP18,155 P2
(45) Date of Patent: Oct. 30, 2007

(54) LAVENDER PLANT NAMED 'D01-24'

(50) Latin Name: *Lavandula stoechas*
Varietal Denomination: D01-24

(75) Inventor: John Robb, Kariong (AU)

(73) Assignee: The Paradise Seed Co. P/L, Kulnura, NSW (AU)

( * ) Notice: Subject to any disclaimer, the term of this patent is extended or adjusted under 35 U.S.C. 154(b) by 0 days.

(21) Appl. No.: 11/450,811

(22) Filed: Jun. 9, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of Lavender plant named 'D01-24', characterized by its compact, upright, outwardly spreading and mounded plant habit; freely branching, dense and bushy plant form; and light pink-colored flowers with showy light pink-colored terminal flower bracts.

1 Drawing Sheet

Botanical designation: *Lavandula stoechas.*
Cultivar denomination: 'D01-24'.

BACKGROUND OF THE INVENTION

The present invention relates to a new and distinct cultivar of Lavender, botanically known as *Lavandula stoechas* and hereinafter referred to by the name 'D10-24'.

The new Lavender is a product of a planned breeding program conducted by the Inventor in Kulnura, New South Wales, Australia. The objective of the breeding program is to create new compact and freely branching Lavender cultivars with large and attractive flowers and good garden performance.

The new Lavender originated from a cross-pollination made by the Inventor in 2000 of the *Lavandula stoechas* cultivar Madrid Pink Improved, disclosed in U.S. Plant Pat. No. 14,205, as the female, or seed, parent with an unknown selection of *Lavandula stoechas,* not patented, as the male, or pollen, parent. The new Lavender was discovered and selected by the Inventor as a single flowering plant with the progeny of the stated cross-pollination grown in a controlled environment in Kulnura, New South Wales, Australia in 1999.

Asexual reproduction of the new cultivar by terminal cuttings at Kulnura, New South Wales, Australia, since 2001, has shown that the unique features of this new Lavender are stable and reproduced true to type in successive generations.

SUMMARY OF THE INVENTION

Plants of the cultivar D01-24 have not been observed under all possible environmental conditions. The phenotype may vary somewhat with variations in environment such as temperature and light intensity without, however, any variance in genotype.

The following traits have been repeatedly observed and are determined to be the unique characteristics of 'D01-24'. These characteristics in combination distinguish 'D01-24' as a new and distinct cultivar:

1. Compact, upright, outwardly spreading and mounded plant habit.
2. Freely branching, dense and bushy plant form.
3. Light pink-colored flowers with showy light pink-colored terminal flower bracts.

Plants of the new Lavender differ from plants of the female parent, the cultivar Madrid Pink Improved, in the following characteristics:

1. Plants of the new Lavender are more compact than plants of the cultivar Madrid Pink Improved.
2. Plants of the new Lavender and the cultivar Madrid Pink Improved differ in petal coloration.

Plants of the new Lavender can be compared to plants of the cultivar Kew Red, not patented. In side-by-side comparisons conducted by the Inventor in Kulnura, New South Wales, Australia, plants of the new Lavender diffused from plants of the cultivar Kew Red in the following characteristics:

1. Plants of the new Lavender were larger than plants of the cultivar Kew Red.
2. Plants of the new Lavender were denser and bushier than plants of the cultivar Kew Red.
3. Plants of the new Lavender and the cultivar Kew Red differed in petal and terminal flower bract coloration as plants of the cultivar Kew Red had dark pink-colored petals and pink-colored terminal flower bracts.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Lavender.

The photograph at the bottom of the sheet comprises a side perspective view of a typical flowering plant of 'D01-24' grown in a one-gallon container.

The photograph at the top of the sheet comprises a close-up view of typical inflorescences of 'D01-24'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the winter and early spring in a polycarbonate-covered greenhouse in Lompoc, Calif. for about 28 weeks in containers. During the production of the plants, day temperatures ranged from 18° to 24° C., night temperatures ranged from 4° to 10° C., and light levels ranged from 4,000 to 8,000 foot-candles.

Botanical classification: *Lavandula stoechas* cultivar D01-24.

Parentage:

*Female parent.*—*Lavandula stoechas* cultivar Madrid Pink Improved, not patented.

*Male parent.*—Unknown selection of *Lavandula stoechas,* not patented.

Propagation:

*Type cutting.*—Terminal vegetative cuttings.

*Time to initiate roots.*—About six days at 23° C.

*Time to produce a rooted young plant, summer.*—About 40 days at 23° C.

*Time to produce a rooted young plant, winter.*—About 50 days at 23° C.

*Root description.*—Fine, fibrous, and freely branching.

Plant description:

*Form.*—Compact, upright, outwardly spreading and mounded plant form. Freely branching, about three main stems each with about six to eight lateral branches; dense and bushy plant habit; moderately vigorous growth habit. Flowers in verticillasters on crowded spikes with showy terminal flower bracts.

*Plant height.*—About 25 cm.

*Plant width.*—About 25 cm.

*Lateral branch description.*—Length: About 18 cm. Diameter: About 5 mm. Internode length: About 1.2 cm. Strength: Strong. Aspect: Mostly upright to outwardly spreading. Texture: Developing stems covered with fine pubescence; older stems, woody. Color, developing stems: 14C. Color, older stems: 177A.

Foliage description:

*Arrangement.*—Opposite, simple; sessile.

*Length.*—About 3 cm.

*Width.*—About 4 mm.

*Shape.*—Linear.

*Apex.*—Acute.

*Base.*—Attenuate, clasping.

*Margin.*—Entire.

*Texture, upper and lower surfaces.*—Pubescence; minute.

*Fragrance.*—Pungent; typical lavender scent.

*Venation pattern.*—Pinnate; reticulate.

*Color.*—Developing foliage, upper and lower surfaces: 137C; venation, 147B. Fully expanded foliage, upper and lower surfaces: More grey than 147A; venation, 147B.

Flower description:

*Flower arrangement and shape.*—Small single flowers in compact verticillasters on crowded spikes. Freely flowering, about 30 open flowers per inflorescence; flowers tubular with five lobes; inflorescences with showy terminal bracts.

*Natural flowering season.*—Continuous throughout the spring. Flower longevity on the plant: Individual inflorescences last about two weeks on the plant and individual flowers last about three days on the plant. Flowers not persistent, terminal flower bracts persistent.

*Flower buds.*—Length: About 8 mm. Diameter: About 2 mm. Shape: Oblong. Color: 75B.

*Inflorescence size.*—Length: About 5.2 cm. Diameter: About 1.6 cm.

*Flowers.*—Length: About 9 mm. Width: About 6 mm. Depth (height): About 4 mm.

*Petals.*—Arrangement: Five, fused into a tube. Length, lobes: About 2 mm. Width, lobes: About 1 mm. Shape: Roughly spatulate. Apex: Rounded. Margin: Entire. Texture, upper and lower surfaces: Smooth, velvety. Color: When opening and fully opened, upper surface: 75B. When opening and fully opened, lower surface: 75B to 75C.

*Terminal flower bracts.*—Arrangement: About four in a single whorl at inflorescence apex. Length: About 2.6 cm. Width: About 1.1 cm. Shape: Obovate to elliptic. Apex: Acute. Base: Attenuate. Margin: Entire. Texture, upper and lower surfaces: Pubescence; minute. Color, immature, upper and lower surfaces: 69A. Color, mature, upper and lower surfaces: 69A.

*Flower bracts.*—Arrangement: Each whorl of flowers subtended by a flower bract. Length: About 1 cm. Width: About 7 mm. Shape: Elliptic. Apex: Acute. Base: Roughly truncate. Margin: Entire. Texture, upper and lower surfaces: Smooth; glabrous. Color, upper and lower surfaces: 147B.

*Calyx.*—Arrangement: Five sepals fused into a short tube with five pointed apices. Length: About 6 mm. Width: About 2 mm. Texture, upper and lower surfaces: Pubescent. Color, upper surface: 147C. Color, lower surface: 147D.

*Peduncle.*—Strength: Strong. Length: About 2.4 cm. Diameter: About 2 mm. Aspect: mostly upright to outwardly spreading. Color: 147C. Texture: Pubescent.

*Reproductive organs.*—Stamens: Quantity per flower: Four. Anther shape: Oval. Anther length: Les than 1 mm. Anther color: 23A. Pollen amount: Scarce. Pollen color: 23A.

*Pistils.*—Quantity per flower: One. Pistil length: About 5 mm. Stigma shape: Rounded. Stigma color: 146C. Style length: About 4 mm. Style color: 155D. Ovary color: 144B.

*Seed/fruit.*—Seed and fruit production has not been observed.

Disease/pest resistance: Plants of the new Lavender have not been noted to be resistant to pathogens and pests common to Lavender.

Garden performance: Plants of the new Lavender have exhibited good tolerance to rain and wind and have been observed to tolerate temperatures from about −2° C. to about 40° C.

It is claimed:

1. A new and distinct Lavender plant named 'D01-24' as illustrated and described.

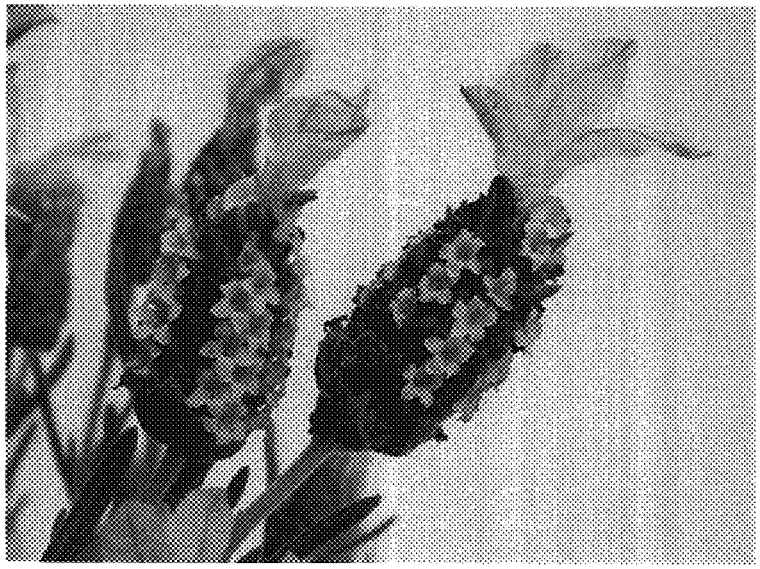
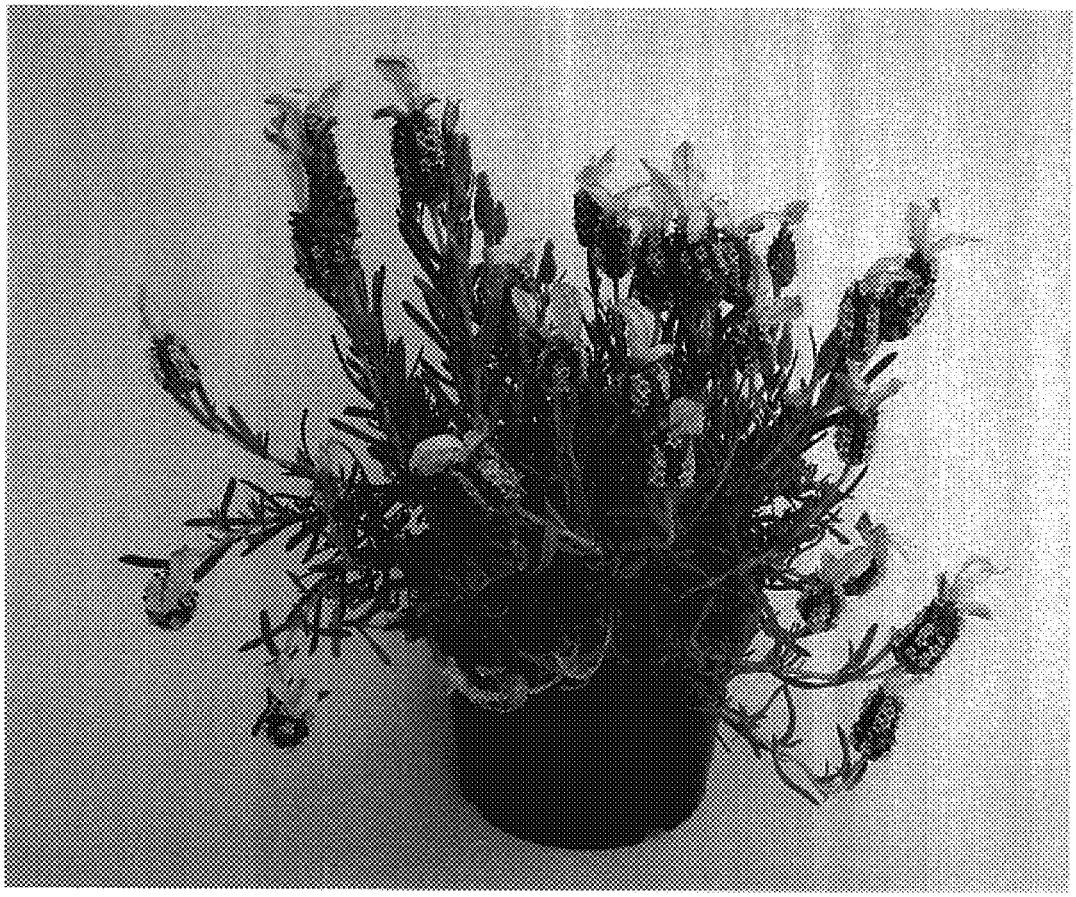

* * * * *